United States Patent [19]

Anderson

[11] E Patent Number: Re. 32,482

[45] Reissued Date of Patent: Aug. 25, 1987

[54] CONNECTOR FOR LIQUID CHROMATOGRAPHY DEVICES

[75] Inventor: James M. Anderson, Arlington Heights, Ill.

[73] Assignee: Alltech Associates, Inc., Deerfield, Ill.

[21] Appl. No.: 906,970

[22] Filed: Sep. 15, 1986

Related U.S. Patent Documents

Reissue of:

[64] Patent No.: 4,586,732
Issued: May 6, 1986
Appl. No.: 581,369
Filed: Feb. 17, 1984

[51] Int. Cl.[4] ..... F16L 19/00

[52] U.S. Cl. ..... 285/12; 285/38; 285/334.2; 285/397

[58] Field of Search ..... 285/89, 334.2, 397, 285/90, 38, 12

[56] References Cited

U.S. PATENT DOCUMENTS

| | | | |
|---|---|---|---|
| 1,680,080 | 8/1928 | Benzion | 285/334.2 X |
| 2,011,433 | 8/1935 | Blagg et al. | 285/334.2 X |
| 2,381,498 | 8/1945 | Iverson | 285/38 |
| 2,699,182 | 1/1955 | Baldridge, Jr. | 285/397 |
| 2,726,104 | 12/1955 | Boitnott et al. | 285/90 |
| 2,755,110 | 7/1956 | Jacobs | 285/423 X |
| 3,231,955 | 2/1966 | Taylor | 285/38 X |
| 3,527,478 | 9/1970 | Enssle | 285/38 |

FOREIGN PATENT DOCUMENTS

| | | | |
|---|---|---|---|
| 29593 | 3/1965 | German Democratic Rep. | 285/89 |

*Primary Examiner*—Thomas F. Callaghan
*Attorney, Agent, or Firm*—Lee, Smith & Zickert

[57] ABSTRACT

A device for connecting one liquid chromatography device to another. The device comprises an elongated, cylindrical shaft having an integral ferrule seat at each end of the shaft. A central bore extends through the shaft and the integral ferrule seats to permit liquid to pass therethrough. An enlarged collar is located centrally on the shaft to aid in attaching the device to chromatography equipment. Because of the short length of the device and minimum size of the central bore, the device has a minimum of interceding volume so that the efficiency of connected devices is uneffected.

4 Claims, 4 Drawing Figures

CONNECTOR FOR LIQUID CHROMATOGRAPHY DEVICES

Matter enclosed in heavy brackets [ ] appears in the original patent but forms no part of this reissue specification; matter printed in italics indicates the additions made by reissue.

BACKGROUND OF THE INVENTION

This invention relates to connecting devices for coupling liquid chromatography equipment, and in particular to a connecting device which permits simple and effective coupling of chromatography equipment with little or no effect on the efficiency of the equipment.

In the field of liquid chromatography, and in particular high pressure liquid chromatography, it is often necessary to couple two or more chromatography columns to one another, or to connect a column to another device, such as a valve. Connecting devices have been developed for effecting such coupling, and typically consist of a length of stainless steel tubing, individual ferrules for each end of the length of the tubing, and threaded fittings which are guided along the tubing and connect the opposite ends of the tubing between adjacent columns or other liquid chromatography equipment which is to be interconnected.

A serious deficiency of the prior art is the fact that the connecting device consists of at least five separate pieces (two end connectors, two ferrules and a length of tubing), which requires a considerable amount of time to complete the coupling. In addition, tools, such as a wrench for tightening the fittings, are required. Finally, because a fairly substantial length of tubing is required to accommodate the fittings and ferrules, the connector adds a certain volume to the equipment which is coupled, thus decreasing the overall efficiency of the coupled equipment.

SUMMARY OF THE INVENTION

The invention overcomes the deficencies of the prior art by providing a connecting device for coupling one liquid chromatography device to another with a minimum of interceding volume. The device comprises an elongated, cylindrical shaft having an integral ferrule seat at each end thereof. A central bore extends through the shaft and the integral ferrule seats for liquid communication between the chromatography devices which are coupled. An enlarged grip is located centrally on the shaft with the grip extending about the shaft to permit attachment of the connecting device without the necessity of tools. Attachment threads are provided on the shaft extending between the grip and the ferrule seats so that the shaft may be directly threaded into a column or other liquid chromatography equipment.

While the grip may be an integral expansion of the shaft, preferrably the grip is removably secured to the shaft. The grip comprises an annular collar which includes a radial bore carrying an adjustable set screw for attaching the collar to the shaft. The shaft may be threaded continuously between the ferrule seats, or the threading may be interrupted at the location to which the annular collar is attached.

As an adjunct to the connecting device, a collet is provided. The collet is threadably secured to the attachment threads at one end of the shaft and is long enough to extend over and beyond the ferrule seat at that end so that the collet may be attached to male threads of a connected chromatography device.

BRIEF DESCRIPTION OF THE DRAWINGS

The invention is shown in greater detail in the accompanying description of an example embodying the best mode of the invention, taken in conjunction with the drawings, in which.

DESCRIPTION OF EXAMPLE EMBODYING BEST MODE OF THE INVENTION

Figure 3:
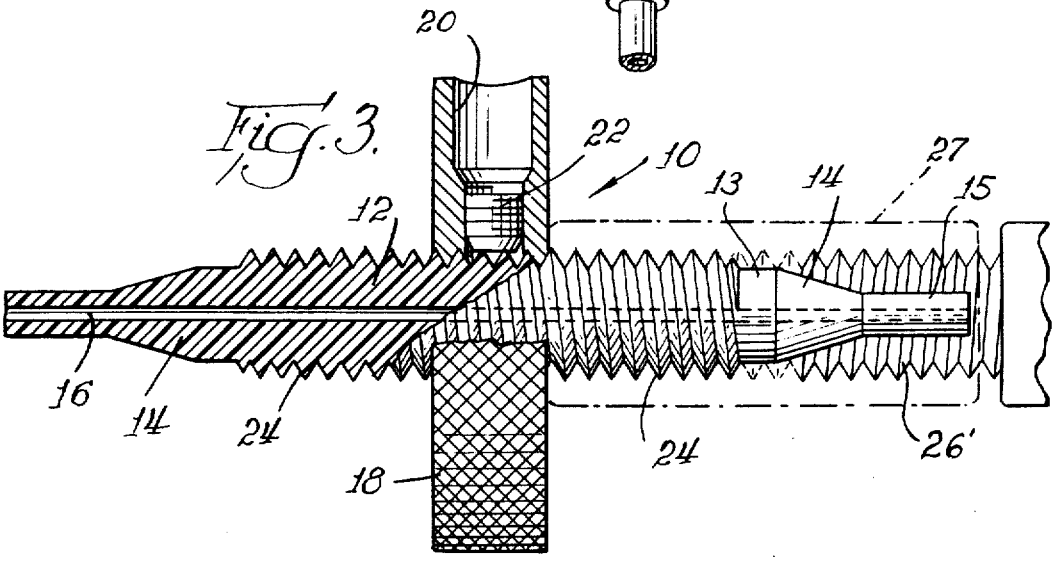
FIG. 3 is an enlarged partial cross-sectional illustration of a connecting device according to the invention showing a collet in phantom when secured to one end of the an externally threaded fitting of a chromatographic device.
Figure 4:
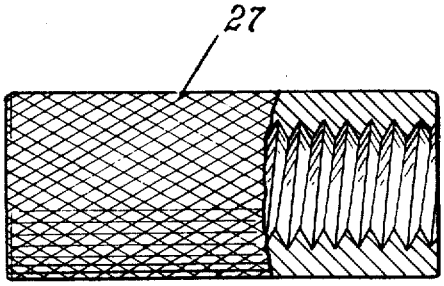
FIG. 4 is an elevational view, partially in cross-section, of the collet.

A connecting device according to the invention is shown generally at 10 in the drawing and is best shown in FIG. 3. The connecting device 10 comprises an elongated, cylindrical shaft or body 12, an integral cylindrical shank portions 13, intergally tapered ferrule seats 14 and a cylindrical pilot portion 15 at each of the shaft 12. A central bore 16 extends through the shaft 12 the shank portions 13, ferrule seats 14 and the pilot portions 15. As seen, the maximum diameter of the ferrule seats 14 is no larger than that of the shaft 12 (or, conversely, the diameter of the shaft 12 is at least as large as that of the ferrule seats 14) to permit attachment to a liquid chromatography device.

An enlarged grip 18 is located centrally on the shaft 12. In the embodiment illustrated, the grip 18 comprises an annular collar including a radial bore 20 having an adjustable set screw 22 for attaching the grip 18 to the shaft 12.

In the embodiment illustrated, the shaft 12 is provided with continuous threads 24 between the opposite ferrule seats 14. It is evident that, if desired or required, the threads 24 need not be continuous and may extend only between a ferrule seat 14 and the grip 18, with that portion of the shaft 12 beneath the grip 18 being unthreaded. For ease of fabrication, normally the threads 24 will extend as shown in FIG. 3.

The connecting device 10 is of a minimum length for coupling two pieces of liquid chromatography equipment. Since the bore 16 is quite small (typically on the order of 0.012 inches in diameter), the connecting device 10 provides a minimum of interceding volume between connected chromatography equipment so that the efficiency of the connected equipment is essentially additive.

Figure 1:
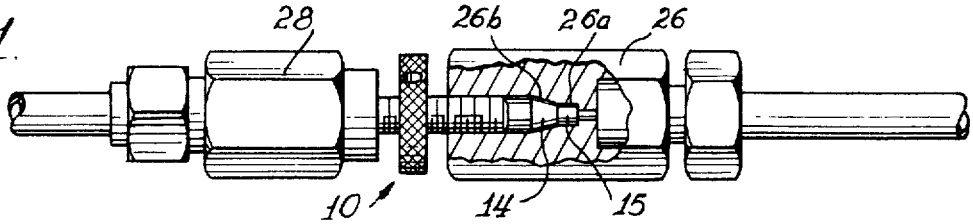
FIG. 1 illustrates the invention when used to couple the internally threaded fittings two liquid chromatography columns, one of which is partially sectioned.

As shown in FIG. 1, when coupled together the externally threaded shaft or body 12 engages the internal threads of the analytical column end fitting 26, the pilot portions 15 enter and substantially fill the counterbore 26a of the end fitting, and the outwardly facing ferrule seat 14 sealingly engages the corresponding tapered inwardly facing seat 26b within the end fitting.

When direct coupling of the connecting device 10 is impossible because the to-be-coupled chromatography equipment has a male-threaded end, the connecting device 10 is provided with a collet 27 as shown. The collet 27 extends over and beyond the ferrule seat 14 to provide a sufficient length to assure a proper connection of the male end fitting 26' of the chromatography equipment to that end of the connecting device 10.

Figure 2:
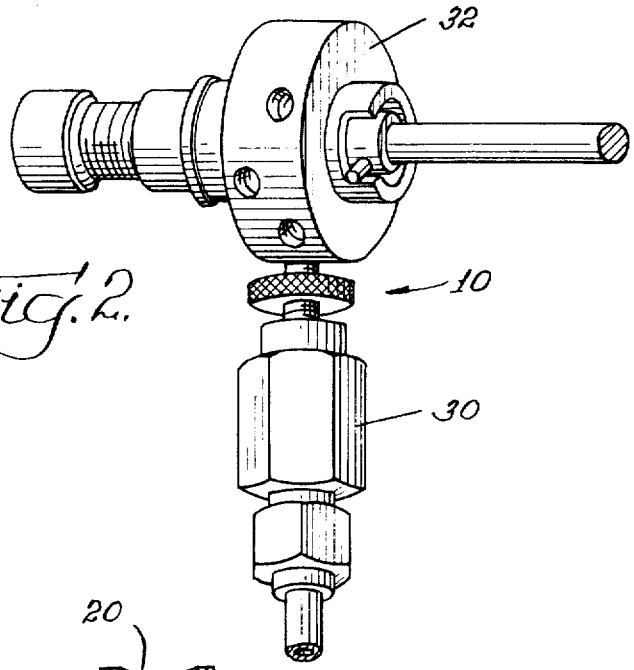
FIG. 2 illustrates the invention when used to couple a liquid chromatography column to a valve.

As is evident, the connecting device 10 can be used to couple many different types of liquid chromatography equipment. Two examples of such coupling are shown in FIGS. 1 and 2. In FIG. 1, the connecting device 10 is shown coupling an analytical column 26 to another column 28, which may be an analytical column or a guard column. In FIG. 2, the connecting device 10 is employed to couple a column 30 to a valve 32.

ACHIEVEMENTS

Because the device 10 is of a minimum length and has a minimal diameter of the bore 16, the bore 16 adds very little interceding volume to coupled chromatography equipment, so that the efficiency of the coupled equipment is not diminished. In fact, due to the extremely small size of the bore 16, the efficiency of coupled columns, such as the columns 26 and 28, is essentially additive, as opposed to prior art column connectors which substantially reduce the efficiency of coupled columns.

The shaft 12 is preferrably made from a highly inert polymer plastic which is soft enough to assure that the ferrule seats 14 will seal coupled columns with the connecting device 10 being only finger tightened. Therefore, the necessity of tools required with prior art column connectors is eliminated.

The unitary construction of the connecting device 10 (with the grip 18 secured to the shaft 12), eliminates the multiple elements of prior art column connectors. Thus, coupling time of the connecting device 10 is significantly reduced, as is the complexity of coupling two items of liquid chromatography equipment.

What is claimed is:

1. A connecting device for interconnecting the threaded end fittings of two liquid chromatography devices in closely adjacent relationship, each end fitting having a throughbore for the passage of liquid therethrough, an axially aligned concentric counterbore and an inwardly tapering, outwardly facing seat, said connecting device comprising an elongated, inert plastic body having a throughbore extending therethrough for the passage of liquids, said body comprising an externally threaded central portion; a pair of cylindrical unthreaded shank portions, a pair of narrow cylindrical pilot portions and a pair of outwardly facing ferrule seats; said cylindrical shank portions being disposed outwardly on opposite sides of said central portion, said cylindrical pilot portions each being disposed at a respective end of said body for extending into and substantially filling the counterbore of the associated chromatography device end fitting, and each of said ferrule seats being disposed intermediate a respective shank portion and pilot portion for sealingly engaging the similarly tapered inwardly facing seat within the associated chromatography device end fitting; and an enlarged grip removably secured to extending outwardly from and circumferentially about the central portion of said body, whereby said grip may be manually manipulated to threadedly engage the threaded end fittings of two liquid chromatography devices and to cause the pilot portions to enter and substantially fill the counterbores of the respective end fittings and the outwardly facing tapered ferrule seats to sealingly engage the correspondingly tapered inwardly facing seats within the respective end fittings.

2. A connecting device according to claim 1 in which said grip comprises an internally threaded annular collar threaded onto the externally threaded central portion of said body, said collar including a radial bore in said collar having an adjustable set screw for attaching said collar to said body central portion.

3. A connecting device according to claim 1 including at least one collet adapted to be threadedly secured to the attachment threads at one end of said body central portion and extending over and beyond one pilot portion, ferrule seat and shank portion at said one end, whereby said connecting device may be connected alternatively to internallythreaded or externally threaded end fittings of liquid chromatography devices.

*4. A connecting device for interconnecting the threaded end fittings of two liquid chromatography devices in closely adjacent relationship, each end fitting having a throughbore for the passage of liquid therethrough, an axially aligned concentric counterbore and an inwardly tapering, outwardly facing seat, said connecting device comprising an elongated, inert plastic body having a throughbore extending therethrough for the passage of liquids, said body comprising an externally threaded central portion; a pair of cylindrical shank portions, a pair of narrow cylindrical pilot portions and a pair of outwardly facing ferrule seats; said cylindrical shank portions being disposed outwardly on opposite sides of said central portion, said cylindrical pilot portions each being disposed at a respective end of said body for extending into and substantially filling the counterbore of the associated chromatography device end fitting, and each of said ferrule seats being disposed intermediate a respective shank portion and pilot portion for sealingly engaging the similarly tapered inwardly facing seat within the associated chromatography device end fitting; and an enlarged grip secured to and extending outwardly from and circumferentially about the central portion of said body, whereby said grip may be manually manipulated to threadedly engage the threaded end fittings of two liquid chromatography devices and to cause the pilot portions to enter and substantially fill the counterbores of the respective end fittings and the outwardly facing tapered ferrule seats to sealingly engage the correspondingly tapered inwardly facing seats within the respective end fittings.*

* * * * *